(12) United States Patent
Kwak

(10) Patent No.: US 9,202,193 B2
(45) Date of Patent: Dec. 1, 2015

(54) EARLY ALERT SYSTEM AND METHOD FOR LIVESTOCK DISEASE DETECTION

(75) Inventor: Sung Bok Kwak, Milpitas, CA (US)

(73) Assignee: Hana Micron America, Inc., Milpitas, CA (US)

( * ) Notice: Subject to any disclaimer, the term of this patent is extended or adjusted under 35 U.S.C. 154(b) by 162 days.

(21) Appl. No.: 13/166,520

(22) Filed: Jun. 22, 2011

(65) Prior Publication Data

US 2012/0326862 A1 Dec. 27, 2012

(51) Int. Cl.
*G06Q 10/08* (2012.01)
*G06Q 50/02* (2012.01)
*A01K 11/00* (2006.01)
*G08B 21/04* (2006.01)

(52) U.S. Cl.
CPC ......... *G06Q 10/0833* (2013.01); *A01K 11/004* (2013.01); *G06Q 50/02* (2013.01); *G08B 21/0423* (2013.01)

(58) Field of Classification Search
CPC ... A01K 11/004; A01K 11/006; G09Q 50/02; G09Q 50/24; G09Q 10/0833
USPC ............ 340/539.12, 573.1, 573.2; 119/14.02, 119/51.02, 51, 712
See application file for complete search history.

(56) References Cited

U.S. PATENT DOCUMENTS

| | | | |
|---|---|---|---|
| 4,618,861 A | 10/1986 | Gettens et al. | |
| 5,873,323 A * | 2/1999 | van den Berg et al. | ..... 119/14.02 |
| 7,543,549 B2 * | 6/2009 | Valencia et al. | ............. 119/174 |
| 7,670,292 B2 | 3/2010 | Haynes | |
| 7,705,736 B1 | 4/2010 | Kedziora | |
| 7,810,451 B2 | 10/2010 | Pratt | |
| 7,931,593 B2 | 4/2011 | Haynes et al. | |
| 8,307,785 B2 * | 11/2012 | Zimmerman et al. | ..... 119/51.02 |
| 8,410,926 B1 * | 4/2013 | Gary et al. | ............... 340/539.12 |
| 2004/0116821 A1 * | 6/2004 | Beiswenger et al. | ......... 600/549 |
| 2007/0288249 A1 * | 12/2007 | Rowe et al. | ........................ 705/1 |
| 2008/0252464 A1 * | 10/2008 | Panasevich | ................ 340/573.1 |
| 2009/0066511 A1 | 3/2009 | Okazaki | |
| 2012/0012069 A1 * | 1/2012 | Hempstead et al. | .......... 119/712 |

* cited by examiner

*Primary Examiner* — Jennifer Mehmood
*Assistant Examiner* — Omar Casillashernandez
(74) *Attorney, Agent, or Firm* — Invent Capture, LLC.; Samuel S. Cho

(57) ABSTRACT

An early alert system and a related method for livestock disease detection are disclosed. In one embodiment of the invention, an activity measurement zone (AMZ) is defined near an incentive device (e.g. food or water dispensing system) with an RFID tag reader, and an animal's entrance into or out of the AMZ is tracked and counted with an RFID tag attached to the animal. If the animals' activity relative to the AMZ drops to an alarmingly low level (e.g. dropping below an alert trigger point) over a period of time, then a user of the alert system is informed of a potential health problem with the animal and may also be encouraged to inspect the animal in person for further determination of its current health and potential medical issues.

17 Claims, 6 Drawing Sheets

An Embodiment of an Early Alert System for Livestock Disease Detection

300

Example of characteristics of an epidemic among animals in a livestock housing

400

Example of an alert trigger point for livestock disease detection

500

EARLY ALERT SYSTEM AND METHOD FOR LIVESTOCK DISEASE DETECTION

BACKGROUND OF THE INVENTION

The present invention generally relates to an early detection of a contagious disease in farm animals. More specifically, the present invention relates to an early alert system and method for livestock disease detection using an radio frequency identification (RFID) reader and an RFID tag assigned to an animal.

Outbreak and control of contagious diseases and epidemics have become an important concern in modern livestock farming industry. As farmers attempt to improve yield and efficiency of their livestock farms within available spaces, animals are often placed in space-constrained livestock housing and are highly susceptible to a rapid contagion of dangerous epidemics. For example, avian influenza outbreaks in chicken farms, mad cow disease in cattle farms, and foot-and-mouth disease outbreaks in various farm animals have become widespread, and early control of these outbreaks have become more difficult as high-efficiency livestock farming are likely causing even faster spread of the diseases among farm animals before any effective quarantine and treatment measures can take effect.

The conventional measure of detecting a disease in farm animals is generally slow and cumbersome. Farmers have to manually monitor conditions of each farm animals, typically contained in a livestock housing, and an animal suspected of being under the influence of a contagious disease is manually checked for its vital signs such as body temperature and heart rate. If this animal is confirmed to be infected of a dangerous or contagious disease, then it may be isolated from the flock for further treatment and handling. This conventional disease detection method is highly dependent on the level of experience and attention of a farmer monitoring the animals, thereby causing some serious medical conditions on a farm animal "slip through" the manual inspection process until the disease is further spread to other nearby animals. Furthermore, the process of checking the vital signs of an ill animal is a serialized, cumbersome, and slow process, and frequently causes delay in moving forward with quarantine, prevention, and/or treatment procedures of remaining animals.

Because any delay in quarantine, prevention, and treatment procedures during an outbreak of a contagious disease in a livestock farm can cause rapid infections to remaining animals, investment losses, and increased health risks to humans, it is highly desirable to devise an early alert system and a method for livestock disease detection. Furthermore, it may also be advantageous to utilize RFID tags attachable to animals for a systematic management of early detection of diseases for farm animals.

SUMMARY

Summary and Abstract summarize some aspects of the present invention. Simplifications or omissions may have been made to avoid obscuring the purpose of the Summary or the Abstract. These simplifications or omissions are not intended to limit the scope of the present invention.

In one embodiment of the invention, an early alert system for livestock disease detection using RFID technology is disclosed. This early alert system comprises an activity measurement zone (AMZ) defined by an RFID signal projection from an RFID tag reader or an RF antenna operatively connected to the RFID tag reader; an incentive device located near or inside the AMZ to encourage an animal attached with an RFID tag to enter and exit the AMZ periodically or frequently; the RFID tag reader configured to read from or write to the RFID tag attached to the animal if the animal is inside the AMZ defined by the RFID signal projection from the RFID tag reader or the RF antenna; a computer server with a CPU and a memory unit operatively connected to the RFID tag reader to receive and transmit information from the RFID tag attached to the animal; and an analytical program module configured to set, adjust, detect, and/or use an alert trigger point for alerting a user that the animal requires personal attention for further medical inspection if an AMZ count for the animal over a period of time drops below the alert trigger point, wherein the analytical program module is executed on the CPU and the memory unit of the computer server.

In another embodiment of the invention, a method of alerting a potential livestock disease to a user of an early alert system is disclosed. This method comprises the steps of: defining an activity measurement zone (AMZ) enabled by an RFID tag reader; attaching an RFID tag to an animal, wherein the RFID tag reader can read from or Write to the RFID tag if the RFID tag is within the AMZ; activating the early alert system for livestock disease detection; monitoring the frequency of the animal's entrance into the AMZ by accessing the RFID tag attached to the animal; and if an alert trigger point is reached, informing the user of the early alert system to encourage further inspection of the animal for a potential health problem or an infection.

DETAILED DESCRIPTION

Figure 1:
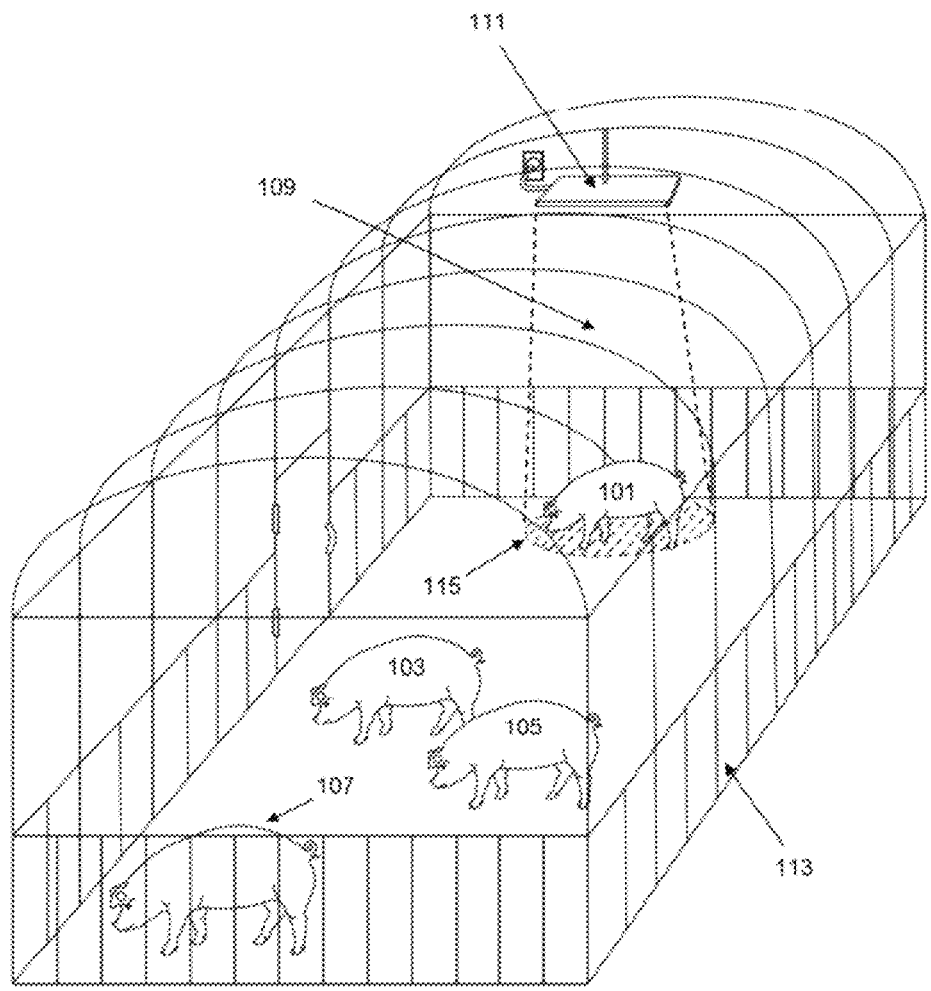
FIG. 1 shows a perspective view of a livestock housing incorporating an early alert system for livestock disease detection, in accordance with an embodiment of the invention.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention.

However, it will be apparent to one of ordinary skill in the art that the invention may be practiced without these specific details. In other instances, well-known features have not been described in detail to avoid unnecessarily complicating the description.

The detailed description is presented largely in terms of description of shapes, configurations, and/or other symbolic representations that directly or indirectly resemble an early alert system and a related method for livestock disease detection. These descriptions and representations are the means used by those experienced or skilled in the art to most effectively convey the substance of their work to others skilled in the art.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment. Furthermore, separate or alternative embodiments are not necessarily mutually exclusive of other embodiments. Moreover, the order of blocks in process flowcharts or diagrams representing one or more embodiments of the invention do not inherently indicate any particular order nor imply any limitations in the invention.

For the purpose of describing the invention, a term "livestock" is defined as farm animals raised for use and/or profit. The term "livestock" can include, but are not limited to, cattle, sheep, pigs, goats, horses, donkeys, mules, and poultry (e.g. chickens, ducks, turkeys, and geese).

Furthermore, for the purpose of describing the invention, a term "activity measurement zone" (AMZ) is defined as a designated area in which the entrance and/or the exit of a monitored animal into the designated area is counted and tracked by an RFID tag and an RFID reading device. In a preferred embodiment of the invention, the RFID reading device is installed on a ceiling of a livestock housing, and has an RFID tag reading aperture projected to a surface of the livestock housing to comprise an activity measurement zone. The activity measurement zone may be situated inside or near a water feed system, a food dispenser system, or another incentive device which encourages an animal to enter the activity measurement zone frequently or periodically.

Moreover, for the purpose of describing the invention, a term "epidemic" and a term "contagious disease" are defined as an infectious disease for animals and/or humans, wherein the infectious disease may spread by physical contact, air, liquid, or another method of disease transmission.

In addition, for the purpose of describing the invention, a term "radio frequency identification," or RFID, is defined as a wireless signal-based identification of a wirelessly-accessible tag, called an "RFID tag" using a wirelessly-accessible tag reader, called "RFID tag reader." In general, an RFID tag contains information which may be written and/or read by the RFID tag reader, an RF antenna operatively connected to the RFID tag reader, or another tag information access device. In a preferred embodiment of the invention, RFID operates in ultra high frequencies (UHF) to achieve longer read/write ranges (e.g. up to several meters) and multiple tag read/write capabilities, which were difficult to achieve in conventional low frequency (LF)-based RFID devices exhibiting shorter read/write ranges (e.g. approximately up to 30 centimeters) and single tag scan functionalities. In a preferred embodiment of the invention, the UHF range for the RFID tag reader is defined by ISO/IEC 18000-6 air interface standard, which utilizes an operating frequency range of 860 MHz~960 MHz. In another embodiment of the invention, the UHF operating frequency range may be defined more broadly as 300 MHz~3 GHz. In general, the conventional LF operating frequencies are below the UHF RFID tag reader operating frequency ranges.

One aspect of an embodiment of the present invention is providing an early alert system for livestock disease detection using RFID technology.

Another aspect of an embodiment of the present invention is providing a method of early detection of livestock disease using RFID technology.

Yet another aspect of an embodiment of the present invention is utilizing a novel concept of an activity measurement zone (AMZ) in conjunction with RFID technology for early detection of livestock disease.

In addition, another aspect of an embodiment of the present invention is providing a motivation, an incentive, or an encouragement for an animal to enter the activity measurement zone frequently or periodically by situating a water feed system, a food dispenser system, or another device near or inside the activity measurement zone.

FIG. 1 shows a perspective view of a caged livestock housing (100) incorporating an early alert system for livestock disease detection, in accordance with an embodiment of the invention. In a preferred embodiment of the invention, farm animals (e.g. 101, 103, 105, 107) are placed inside the caged livestock housing (100) with a defined or fenced perimeters (113). In the preferred embodiment of the invention, the farm animals (e.g. 101, 103, 105, 107) are depicted as pigs. In another embodiment of the invention, the farm animals may be cattle, sheep, pigs, goats, horses, donkeys, mules, poultry (e.g. chickens, ducks, turkeys, and geese), or another appropriate farm animal.

In the preferred embodiment of the invention, the early alert system for livestock disease detection includes an RFID tag reader (111) with an integrated RF antenna installed on a ceiling of a livestock housing (e.g. 100), an activity measurement zone (AMZ) (115) defined by an aperture of the RFID tag reader (111), and its corresponding RFID signal projection (109). In one embodiment of the invention, the early alert system for livestock disease detection may also include an RF antenna operatively connected to the RFID tag reader (111), a server processing RFID tag information, and/or another wireless tag information processing device. In one or more embodiments of the invention, it may be desirable to use a discrete RF antenna instead of the integrated RF antenna in the RFID tag reader (e.g. 111) to define the activity measurement zone (AMZ) (e.g. 115). In one embodiment of the invention, the AMZ (115) may be defined on a floor of a livestock housing. In another embodiment of the invention, the AMZ (115) may be defined on another surface other than the floor.

In a preferred embodiment of the invention, the RFID tag reader (111) has an integrated RF antenna for enabling communication with one or more RFID tags. In another embodiment of the invention, an RFID tag reader may be operatively connected to a discrete RF antenna which enables communication with one or more RFID tags. Yet in another embodiment of the invention, an RFID tag reader may be operatively connected to a plurality of discrete RF antennas. Furthermore, in one embodiment of the invention, the RFID tag reader (111) may be a fixed unit with an integrated RF antenna or a discrete RF antenna operatively connected to an RFID tag reader. In another embodiment of the invention, an RFID tag reader may be a portable unit with an integrated RF antenna.

Furthermore, in one example, the activity measurement zone (AMZ) is a circular area (i.e. 115) defined by a projected diameter of the RFID signal projection (109) from the RFID tag reader (111). In another example, the AMZ may be an ellipse, a square, a polygonal, or any other shapes also defined by projected length and/or height of the RFID signal projection (109). In the preferred embodiment of the invention, the RFID signal projection (109) is invisible to a naked human eye as any radio frequency wave is invisible to humans, and the corresponding AMZ (115) is also invisible to the naked human eye. However, visual markers such as painted borders or elevated objects may be used to help farmers visualize where the AMZ (115) is located per livestock housing.

Figures 6, 7A, 7B:
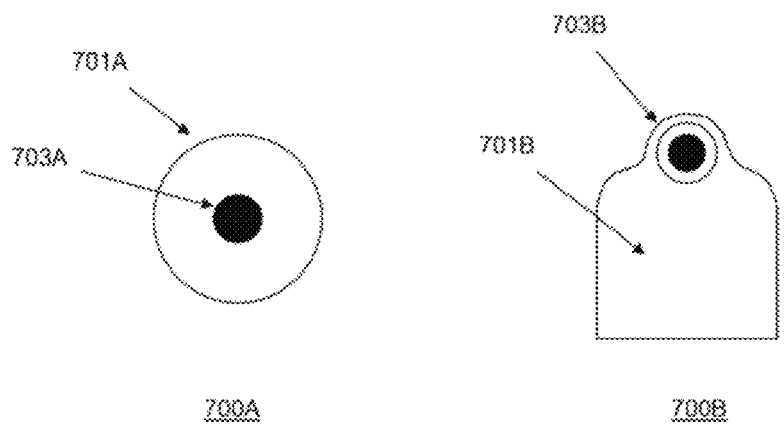
FIG. 6 shows an example of information stored in an RFID tag attachable to an animal, in accordance with an embodiment of the invention.
FIG. 7A shows an example of an RFID tag attachable to an animal in accordance with an embodiment of the invention.
FIG. 7B shows another example of an RFID tag attachable to an animal in accordance with an embodiment of the invention.

Continuing with FIG. 1, in the preferred embodiment of the invention, the RFID tag reader (111) is powered by an AC electric outlet. In one or more embodiments of the invention, the RFID tag reader (111) may be powered by a battery or a source of alternative energy, such as a solar panel or a wind turbine. In the preferred embodiment of the invention, the RFID tag reader (111) with an integrated RF antenna is capable of reading information from an RFID tag attached to a farm animal (e.g. 101) when the farm animal (e.g. 101) enters the activity measurement zone (AMZ) (115). The RFID tag reader (111) may also be capable of writing information to the RFID tag attached to the farm animal (e.g. 101) when the farm animal (e.g. 101) enters the AMZ (115). An example of information read from or written to a particular RFID tag attached to a particular farm animal may include, but are not limited to, a tag ID, an animal type, date of birth, gender, owner, vaccine records, AMZ count, and/or other information as illustrated by FIG. 6, which shows an example of information stored in an RFID tag attached to a farm animal.

In the preferred embodiment of the invention, the RFID tag reader (111) and RFID tags attachable to farm animals are designed to operate in UHF frequencies, which enable longer-range access (e.g. up to several meters) between the RFID tag reader (111) and RFID tags than the conventional low frequency (LF)-based RFID solutions, which can typically access the tags in less than 30 centimeters. Furthermore, the RFID tag reader (111) and corresponding RFID tags, which are designed to operate in UHF frequencies, can handle simultaneous multiple RFID tag reads and writes, thereby enabling the implementation of the AMZ (115) for tracking simultaneous entry and exit of a multiple number of farm animals (e.g. 101, 103, 105, 107) in accordance with an embodiment of the invention.

In one or more embodiments of the invention, the activity measurement zone (AMZ) (e.g. 115) is a designated area in which the entrance and/or the exit of a monitored animal into the designated area is counted and tracked by an RFID tag and an RFID reading device (e.g. 111). In a preferred embodiment of the invention, the RFID reading device (e.g. 111) with an integrated RF antenna or a discrete RF antenna operatively connected to a RFID reading device is installed on a ceiling of a livestock housing (e.g. 100), and has an RFID tag reading aperture projected (e.g. 109) to a surface of the livestock housing to formulate an activity measurement zone (AMZ) (e.g. 115). The activity measurement zone (AMZ) (e.g. 115) may be situated inside or near a water feed system, a food dispenser system, or another incentive device which encourages an animal to enter the activity measurement zone frequently or periodically.

Figure 2:
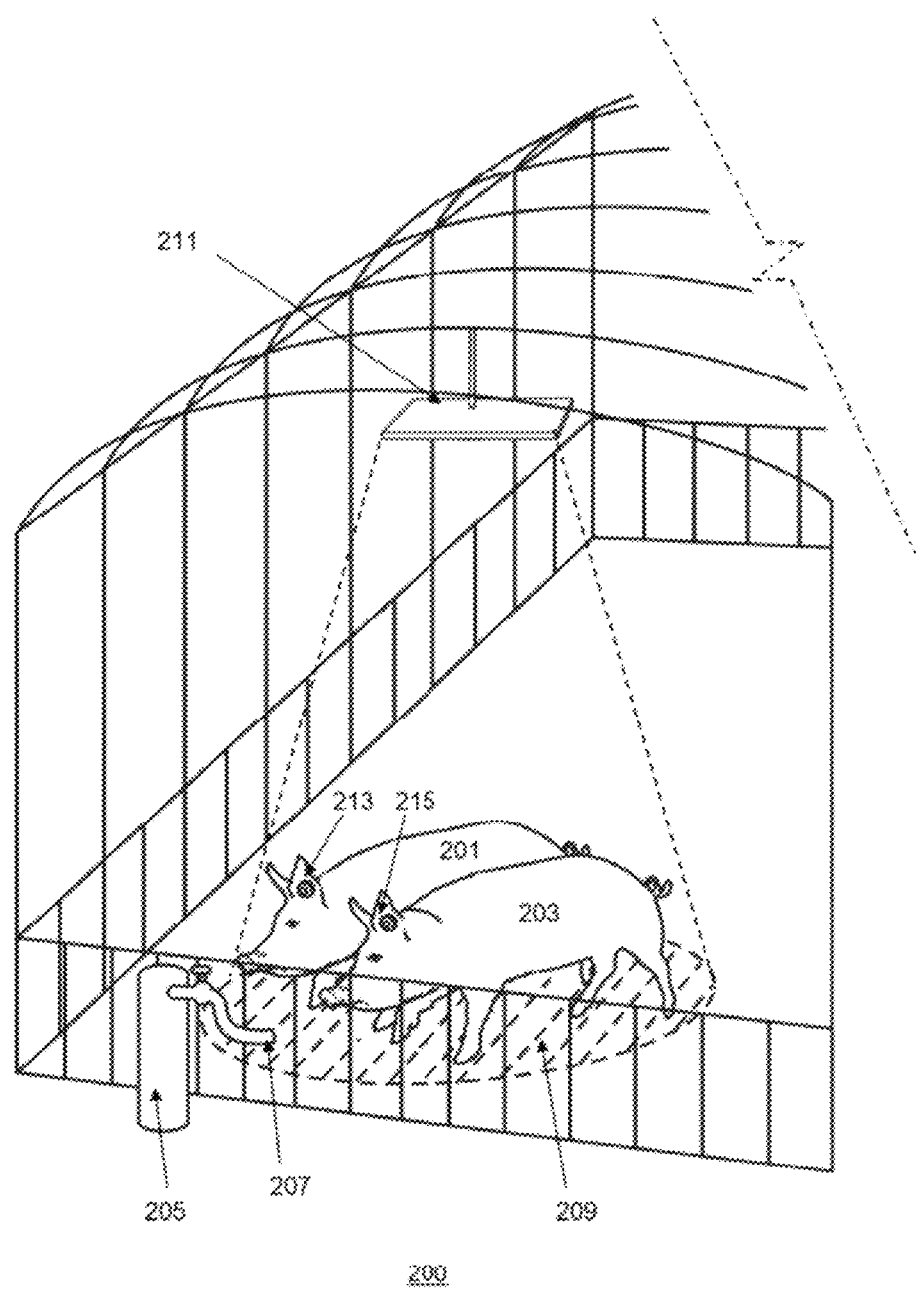
FIG. 2 shows a partial perspective view of a livestock housing incorporating an early alert system for livestock disease detection, in accordance with an embodiment of the invention.

FIG. 2 shows a partial perspective view of a livestock housing (200) incorporating an early alert system for livestock disease detection, in accordance with an embodiment of the invention. In a preferred embodiment of the invention, the early alert system for livestock disease detection can track and count entry and exit of each farm animal (e.g. 201, 203) entering and exiting an activity measurement zone (AMZ) (e.g. 209) by reading and/or writing each RFID tag (e.g. 213, 215) attached to each farm animal (e.g. 201, 203) in the livestock housing with an RFID tag reader (e.g. 211) installed inside or near the livestock housing. In one embodiment of the invention, the early alert system for livestock disease detection may also include an RF antenna integrated into an RFID tag reader or a discrete RF antenna operatively connected to an RFID tag reader. In addition, the early alert system for livestock disease detection may also include a server processing RFID tag information, and/or another wireless tag information processing device.

In a preferred embodiment of the invention, the RFID tag reader (211) has an integrated RF antenna for enabling communication with one or more RFID tags. In another embodiment of the invention, an RFID tag reader may be operatively connected to a discrete RF antenna which enables communication with one or more RFID tags. Yet in another embodiment of the invention, an RFID tag reader may be operatively connected to a plurality of discrete RF antennas, wherein the plurality of discrete RF antennas defines an activity measurement zone (AMZ) (e.g. 209) to access one or more RFID tags entering and/or exiting the AMZ. Furthermore, in one embodiment of the invention, the RFID tag reader (211) may be a fixed unit with an integrated RF antenna or a discrete RF antenna operatively connected to a RFID tag reader. In another embodiment of the invention, an RFID tag reader may be a portable unit with an integrated RF antenna.

In one or more embodiments of the invention, it may be desirable to also install an incentive device (e.g. 207) inside or near the AMZ (e.g. 209), because the incentive device (e.g. 207) motivates a farm animal to enter the AMZ (e.g. 209) frequently or periodically.

Farm animals which are anemic and/or less active over a particular period of time may indicate that they are getting sick and/or require medical attention. A novel aspect of the early alert system and method for livestock disease detection is related to farm animals' general tendency to become more inactive if they are getting sick. Therefore, an animal's sudden or gradual drop in its activity level near an incentive (e.g. food, water, and etc.) can be a good indication of its deteriorating health. By utilizing an RFID tag reader (e.g. 211) capable of simultaneous multiple RFID tag (e.g. 213, 215) accesses on farm animals (e.g. 201, 203) in a defined area (e.g. AMZ (209) of FIG. 2, AMZ (115) of FIG. 1, and etc.) with an incentive device (e.g. 207) inside or nearby, one or more embodiments of the present invention disclose a unique and novel system and a related method, which enable an early and proactive detection of a farm animal's onset of disease or sickness.

One or more embodiments of the present invention may be particularly useful for alerting a farmer for a potentially-infectious disease on a particular farm animal attached with an RFID tag based on its reduced activity levels to the activity measurement zone (AMZ) (e.g. 209). The early alert system and method may alert the farmer by a periodic communication method such as a periodic email report (i.e. hourly, daily, weekly, and etc.) or by dynamic event triggers. In dynamic event trigger instances, an e-mail, a telephone call, a text message, a display terminal alert, or any other desirable dynamically-triggered alert methods may be triggered by an alarming event, such as reaching an alert trigger point for a particular animal attached with an RFID tag.

In the particular example illustrated in FIG. 2, farm animals are depicted as pigs (201, 203), each of which has an RFID tag (213, 215) attached to its ear. Furthermore, the incentive device (207) held up by an incentive device stand (205) is situated near or inside the activity measurement zone (AMZ)

(209). In a preferred embodiment of the invention, the incentive device (207) may be a water feed system or a food dispenser system. In another embodiment of the invention, the incentive device (207) may be another incentive apparatus which motivates the farm animals to enter the AMZ (209) frequently or periodically.

Continuing with FIG. 2, in the preferred embodiment of the invention, the RFID tag reader (211) is capable of reading information from an RFID tag (213, 215) attached to a farm animal (201, 203) when the farm animal (e.g. 101) enters the activity measurement zone (AMZ) (115). Furthermore, the RFID tag reader (211) may also be capable of writing information to the RFID tag attached to the farm animal (201, 203) when the farm animal (201, 203) enters the AMZ (209). An example of information read from or written to a particular RFID tag attached to a particular farm animal may include, but are not limited to, a tag ID, an animal type, date of birth, gender, owner, vaccine records, AMZ count, and/or other information as illustrated by FIG. 6, which shows an example of information stored in an RFID tag attached to a farm animal.

In the preferred embodiment of the invention, the RFID tag reader (211) and RFID tags attachable to farm animals are designed to operate in UHF frequencies, which enable longer-range access (e.g. up to several meters) between the RFID tag reader (211) and RFID tags than the conventional low frequency (LF)-based RFID solutions, which can typically access the tags in less than 30 centimeters. Furthermore, the RFID tag reader (211) and corresponding RFID tags (213, 215), which are designed to operate in UHF frequencies, can handle simultaneous multiple RFID tag reads and writes, thereby enabling the implementation of the AMZ (209) for tracking simultaneous entry and exit of a multiple number of farm animals (201, 203) in accordance with an embodiment of the invention.

Figure 3:
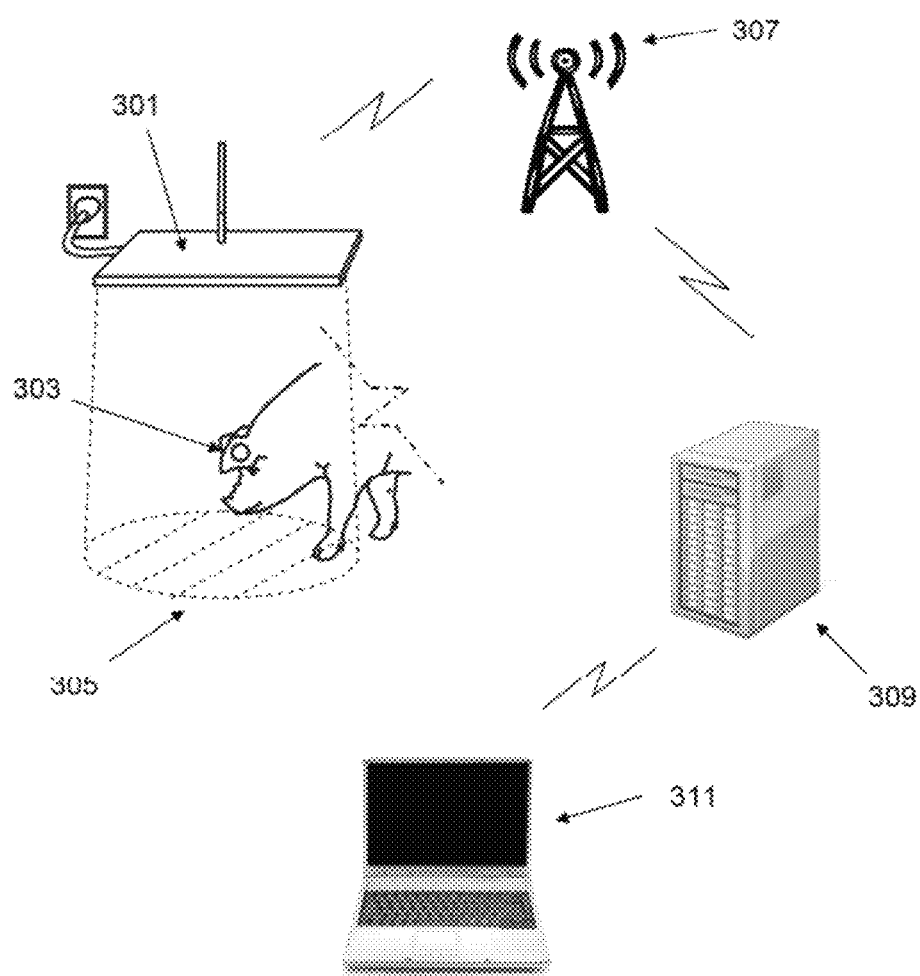
FIG. 3 shows a system diagram for an early alert system for livestock disease detection, in accordance with an embodiment of the invention.

FIG. 3 shows a system diagram for an early alert system (300) for livestock disease detection, in accordance with an embodiment of the invention. In a preferred embodiment of the invention, the early alert system (300) for livestock disease detection comprises an RFID tag reader (301), an activity measurement zone (AMZ) (305), an RFID tag (303) operatively attached to an animal, a wireless transceiver (307) (e.g. a WiFi transceiver, a cellular base station, another wireless protocol transceiver, or a combination thereof) operatively connected to the RFID tag reader (301), and a computer server (309) configured to process, display, and/or store RFID tag-related information, wherein the computer server (309) also contains an analytical program module to set, adjust, detect, and/or use an alert trigger point for alerting a user that the animal requires personal attention for further inspection and determination of its health.

The early alert system (300) may also further comprise a user display terminal (311) configured to display useful information to the user (e.g: farmer). Furthermore, the early alert system (300) may also utilize an email alert, a telephone call, and/or a text message to alert the farmer that the alert trigger point is reached for a potential livestock disease on the animal with the RFID tag (303).

In the preferred embodiment of the invention, the alert trigger point is reached if the animal's activity measurement zone (AMZ) entry count drops dramatically over a period of time, and/or is less than what is considered a healthy amount of activity to the AMZ. Furthermore, in the preferred embodiment of the invention, the analytical program module is a software program, which receives information (e.g. one or more items in FIG. 6) from the RFID tag (303) or transmits information (e.g. one or more items in FIG. 6) to the RFID tag (303). This software program may be configured to be executed on a CPU and a memory unit of the computer server (309).

In one or more embodiments of the invention, the communication among the RFID tag reader (e.g. 301), the computer server (309), and the user display terminal (311) may be implemented using at least some wired connections for device communications, instead of only utilizing wireless communications. Therefore, one or more embodiments of the invention may not require the wireless transceiver (e.g. 307), if the communication points between the RFID tag reader (e.g. 301) and the computer server (e.g. 309) are based on wired lines.

Furthermore, in one or more embodiments of the invention, the user display terminal (e.g. 311) may be a desktop or a laptop computer, which may also optionally integrate the functionality of a separate computer server (e.g. 309), thereby making the separate computer server (e.g. 309) unnecessary in their respective implementations. In addition, in one or more embodiments of the invention, an RF antenna may be operatively connected to the RFID tag reader (e.g. 301) to read from or write to the RFID tag (e.g. 303). Yet in another embodiment of the invention, an RF antenna which can read from or write to the RFID tag (e.g. 303) may be operatively connected to the computer server (e.g. 309) and/or the user display terminal (e.g. 311), wherein the computer server (e.g. 309) and/or the user display terminal (e.g. 311) integrate the functionality of an RFID tag reader (e.g. 301).

Continuing with FIG. 3, in one or more embodiments of the invention, it may be desirable to also install an incentive device (e.g. 207 of FIG. 2) inside or near the AMZ (e.g. 305), because the incentive device (e.g. 207 of FIG. 2) motivates a farm animal to enter the AMZ (e.g. 305) frequently or periodically. Farm animals which are anemic and/or less active over a particular period of time may indicate that they are getting sick and/or require medical attention. A novel aspect of the early alert system and method for livestock disease detection is related to farm animals' general tendency to become more inactive if they are getting sick. Therefore, an animal's sudden or gradual drop in its activity level near an incentive (e.g. food, water, and etc.) can be a good indication of its deteriorating health. By utilizing an RFID tag reader (e.g. 301) capable of simultaneous multiple RFID tag (e.g. 303, etc.) accesses on farm animals in a defined area (e.g. AMZ (305)) with an incentive device (e.g. 207 of FIG. 2) inside or nearby, one or more embodiments of the present invention disclose a unique and novel system and a related method, which enable an early and proactive detection of a farm animal's onset of disease or sickness. One or more embodiments of the present invention may be particularly useful for alerting a farmer for a potentially-infectious disease on a particular farm animal attached with an RFID tag (e.g. 303) based on its reduced activity levels to the activity measurement zone (AMZ) (e.g. 305).

Figure 4:
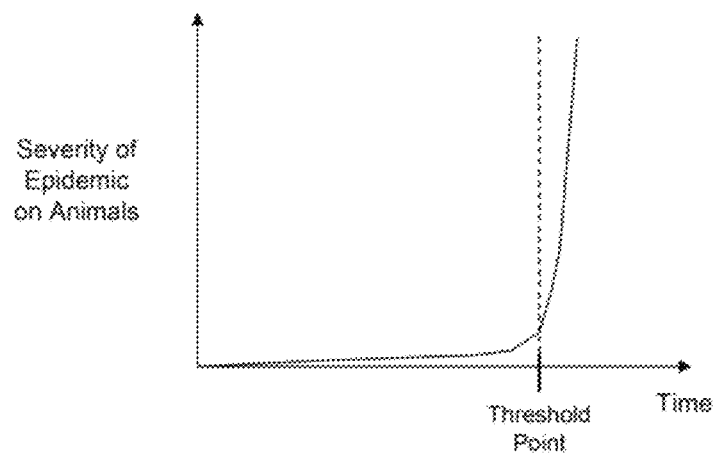
FIG. 4 shows an example of characteristics of an epidemic among animals in a livestock housing.

The importance of early detection of an infectious livestock disease is illustrated in FIG. 4. FIG. 4 shows an example (400) of characteristics of an epidemic among animals in a livestock housing, in accordance with an embodiment of the invention. In this example, the severity of epidemic on animals is graphed against time after the start of an infection on a first infected animal. The epidemic starts with a single infected animal, but begins to spread exponentially as the number of infected animals multiplies in the livestock housing. A "threshold point" relative to the progression of time is shown to illustrate that there comes a point of "no return," or a starting point for a very difficult epidemic containment in the livestock housing, if the epidemic is accidentally left unnoticed and/or untreated.

Therefore, the novel early alert system and method for livestock disease detection as shown in various embodiments of the present invention may become a very helpful tool for farmers to detect, control, and treat any outbreak of infectious diseases earlier and more accurately than manual inspection of the farm animals. The novel early alert system and method for livestock disease detection may be especially useful in containing potential damages and preventing further outbreak of an infectious disease, if an early alert for a potential outbreak of the infectious disease is given to a farmer well before the threshold point of "no return," as shown in FIG. 4.

Figure 5:
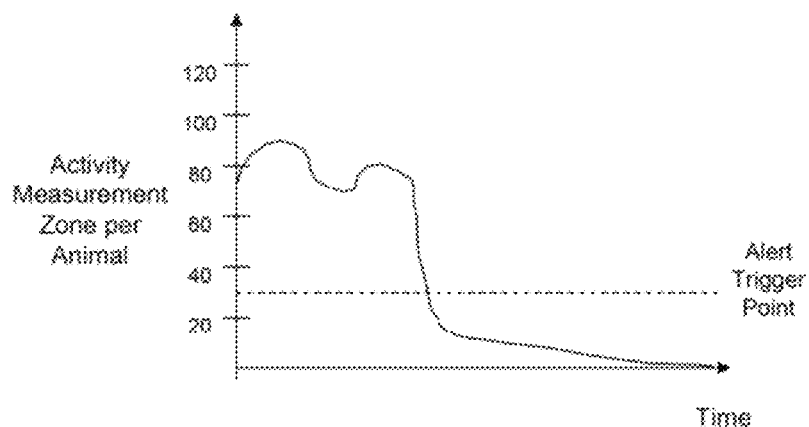
FIG. 5 shows an example of an alert trigger point for livestock disease detection, in accordance with an embodiment of the invention.

FIG. 5 shows an example (500) of an alert trigger point for livestock disease detection in accordance with an embodiment of the invention. This example shows an activity measurement zone per animal plotted against a progression of time, as shown by the graph. In this particular example, an animal with an RFID tag is tracked for its entry and exit into an activity measurement zone (AMZ) Over a period of one week. For the first few days, the animal showed a normal level of activity in and out of the AMZ (e.g. 70~90 entries into the AMZ). Then, the animal's activity level in and out of the AMZ suddenly drops to an alarming level, which is exemplified by crossing of the "alert trigger point" when the animal's activity into the AMZ falls below 30 entries per day.

In a preferred embodiment of the invention, the early alert system and method for livestock disease detection keeps track of activity levels of each animal with an RFID tag, and an animal with an AMZ-related activity level falling below the alert trigger point is flagged as a potential health problem worthy of a farmer's attention. It should be noted that reaching the alert trigger point does not necessarily mean that the animal in question is sick. For example, the alert trigger point may be reached as a result of an equipment-related false alarm, or unusual circumstances without any outbreak of a disease. However, a sudden or unusual drop in an animal's AMZ-related activity level strongly indicates that a health problem likely caused the animal's reduction in activity, and a system-level alert for a closer personal inspection of the animal in question is justified for proactive prevention, detection, and management of livestock diseases.

In the preferred embodiment of the invention, the tracking of activity levels of each animal with an RFID tag is coordinated and managed by an analytical program module, which is configured to set, adjust, detect, and/or use an alert trigger point for alerting a user that a particular animal requires personal attention for further inspection and determination of its health.

In one exemplary use of the analytical program module, the analytical program may use statistical methods to calculate and determine what is a good alert trigger point. In another exemplary use of the analytical program module, the analytical program may allow a user (e.g. a farmer) to manually choose an alert trigger point based on a cutoff value for activity levels per day, week, or another defined period of time. In one or more embodiments of the invention, the analytical program module may reside in a computer server (e.g. 309 of FIG. 3), a desktop computer, and/or a laptop computer.

If the alert trigger point is reached for a particular animal, as shown in FIG. 5, the early alert system may alert the user via a user display terminal (e.g. 311 of FIG. 3). Furthermore, the early alert system may also utilize an email alert, a telephone call, and/or a text message to alert the user proactively that the alert trigger point is reached for further personal attention to the particular animal. For example, in one embodiment of the invention, the early alert system may generate the email alert first, and then also proceed to the telephone call-based alert if necessary.

FIG. 6 shows an example of information (600) stored in an RFID tag attachable to an animal, in accordance with an embodiment of the invention. In a preferred embodiment of the invention, an RFID tag attachable to a particular animal stores a unique tag identification code (601) designed to identify the particular animal among a plurality of animals. The unique tag identification code (601) for the particular animal is also typically associated with other pieces of information, such as a type/grade of the animal (603), date of birth (605), gender (607), owner (609), and vaccine records (611) for the particular animal. In addition, the RFID tag may also keep records of castration because the completion of castration may impact a particular animal's behavior.

Furthermore, in one or more embodiments of the invention, an activity measurement zone (AMZ) count (613) is also tracked, updated, and associated with the particular animal identified by the unique tag identification code (601). In one embodiment of the invention, tracking and updating the AMZ count (613) may be a task of an analytical program module, which is also responsible for setting, adjusting, detecting, and/or using an alert trigger point for alerting a user that the particular animal requires personal attention for further inspection and determination of its health. In another embodiment of the invention, tracking and updating the AMZ count (613) may be a task of another software and/or hardware module which communicates with the analytical program module. In one or more embodiments of the invention, the AMZ count (613) may be incremented by one for each entry of the particular animal into the AMZ. In addition, the AMZ count (613) may be periodically reset to an initialization value on a daily, weekly, or another period-defined basis, depending on a particular embodiment of the invention. In the preferred embodiment of the invention, if the AMZ count (613) within a particular period (e.g. daily, weekly, and etc.) for a particular animal (e.g. A00001) falls below the alert trigger point, then the user is alerted via a user display terminal, a phone call, an email alert, and/or a text message.

Continuing with FIG. 6, information (600) stored in an RFID tag attachable to an animal may also include other information (615) not shown in FIG. 6. In a preferred embodiment of the invention, the RFID tag per animal may be initialized with a fixed set of information, such as a unique tag identification code (601), a type/grade of the animal (603), date of birth (605), gender (607), and owner (609), while other pieces of information such as vaccine records (611) and AMZ counts (613) may be periodically or continuously updated throughout the lifetime of a particular animal. Furthermore, some or all pieces of information (600) can be read from or written to the RFID tag periodically or continuously throughout the lifetime of the particular animal for use by the analytical program module and/or other relevant modules, devices, and apparatuses to enable the early alert system for livestock disease detection.

FIG. 7A shows an example of a circular RFID tag (700A) attachable to an animal in accordance with an embodiment of the invention. The circular RFID tag (700A) is typically used for a smaller animal such as a pig. In a preferred embodiment of the invention, the circular RFID tag (700A) is a battery-less (i.e. without a battery) "passive" tag, which comprises a non-volatile memory unit and an RF antenna encapsulated by a weather-resistant covering (701A). In the preferred embodiment of the invention, the circular RFID tag (700A) has a diameter of 3.5 centimeters. The RF antenna in the circular RFID tag (700A) is configured to receive an electromagnetic signal from an RFID tag reader to energize the non-volatile memory unit inside the circular RFID tag (700A) to transmit information from or send information to the non-volatile memory unit. In another embodiment of the invention, the circular RFID tag (700A) may be a battery-powered "active" tag.

In the preferred embodiment of the invention, the circular RFID tag (700A) also has an attachment pin mechanism (703A) to enable a secure attachment of the circular RFID tag (700A) to an ear or another body part of an animal. Furthermore, the weather-resistant covering (701A) is generally made of sturdy plastic, rubber, and/or other synthetic materials which are non-poisonous for use with edible livestock.

FIG. 7B shows an example of a rectangular RFID tag (700B) attachable to an animal in accordance with an embodiment of the invention. The rectangular RFID tag (700B) can be used in a variety of animals, but most notably, cattle. In a preferred embodiment of the invention, the rectangular RFID tag (700B) is a battery-less "passive" tag, which comprises a non-volatile memory unit and an RF antenna encapsulated by a weather-resistant covering (701B). The RF antenna in the rectangular RFID tag (700B) is configured to receive an electromagnetic signal from an RFID tag reader to energize the non-volatile memory unit inside the rectangular RFID tag (700B) to transmit information from or send information to the non-volatile memory unit. In another embodiment of the invention, the rectangular RFID tag (700B) may be a battery-powered "active" tag.

In the preferred embodiment of the invention, the rectangular RFID tag (700B) also has an attachment pin mechanism (703B) to enable a secure attachment of the rectangular RFID tag (700B) to an ear or another body part of an animal. Furthermore, the weather-resistant covering (701B) is generally made of sturdy plastic, rubber, and/or other synthetic materials which are non-poisonous for use with edible livestock.

Figure 8:
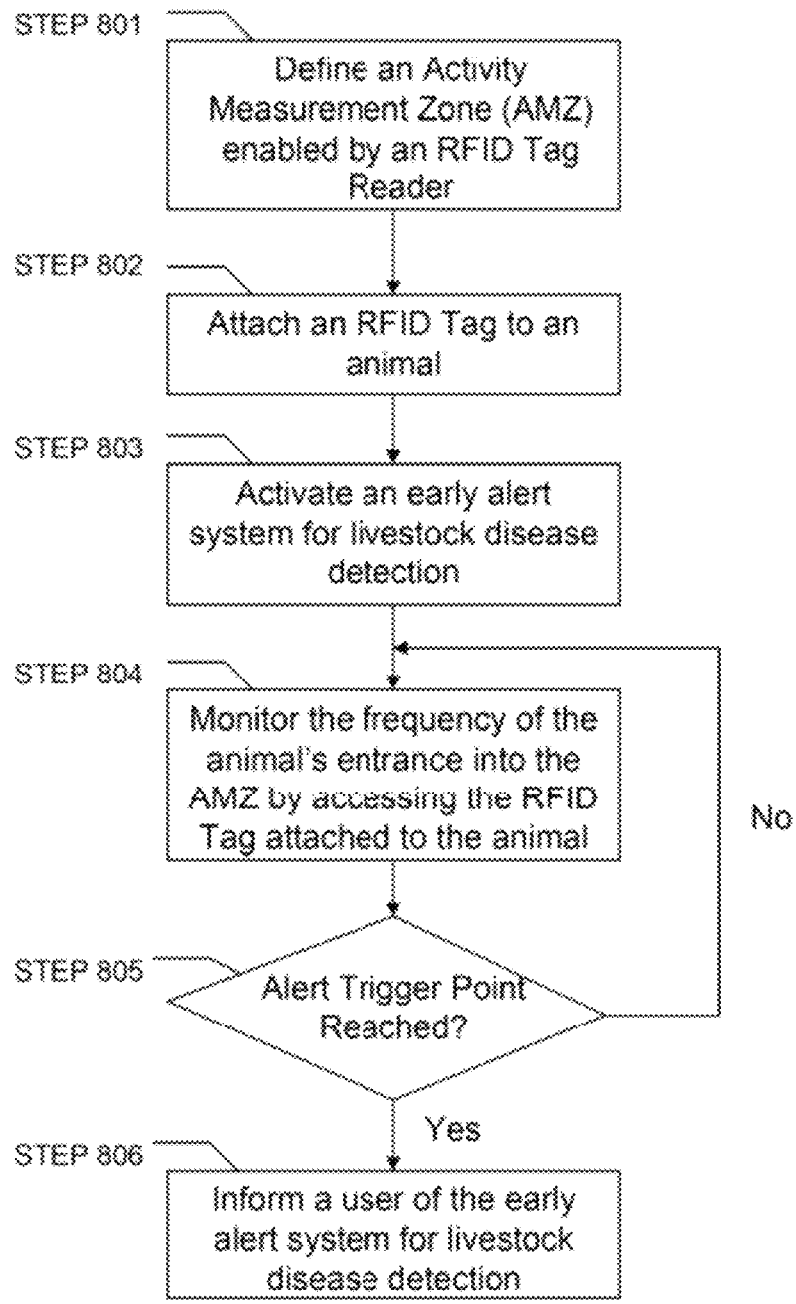
FIG. 8 shows a method of using an early alert system for livestock disease detection in accordance with an embodiment of the invention.

FIG. 8 shows a method (800) of using an early alert system for livestock disease detection in accordance with an embodiment of the invention. In a preferred embodiment of the invention, a user (e.g. a farmer) can define an activity measurement zone (AMZ) enabled by an RFID tag reader, as shown in STEP 801. Then, the user may attach an RFID tag to an animal, as shown in STEP 802. In one example, the RFID tag may be attached to an ear of the animal. In another example, the RFID tag may be attached to another body part of the animal. In most cases, data initialization of the RFID tag may be necessary prior to or during the attachment of the RFID tag to the animal. Then, the user can activate an early alert system for livestock disease detection, as shown in STEP 803. In a preferred embodiment of the invention, the early alert system for livestock disease detection may resemble a system architecture shown in FIG. 3. In another embodiment of the invention, the early alert system for livestock disease detection may incorporate at least partially wireline-based connections and/or other devices.

The early alert system for livestock disease detection, once activated, begins to monitor the frequency of the animal's entrance into the activity measurement zone (AMZ) by accessing the RFID tag attached to the animal, as shown in STEP 804. In one embodiment of the invention, the early alert system tracks and counts the number of entrances to the AMZ per animal over a defined period of time by recognizing a unique tag identification code (e.g. 601) per each animal. The early alert system may store relevant data in a computer or a computer server. Furthermore, the RFID tag attached to the animal may also optionally store an AMZ entrance count, as previously shown by an AMZ count field (e.g. 613 in FIG. 6), if the RFID tag reader is configured to conduct a data field update function to store the AMZ entrance count for the RFID tag.

Continuing with FIG. 8, if an alert trigger point is reached because the AMZ count for a particular animal drops below the alert trigger point for a defined period of time, then the early alert system for livestock disease detection informs the user that personal attention is necessary to inspect the particular animal in question to determine its potential health problems, as shown in STEP 806. On the other hand, if the alert trigger point is not reached during the monitoring phase of the animal's entrance into the AMZ, then the early alert system continues to monitor the frequency of the animal's entrance into the AMZ by accessing the RFID tag attached to the animal, as shown in STEPs 804 and 805.

One or more embodiments of the early alert system and method for livestock disease detection have been illustrated in FIGS. 1~8 and described above. The present invention provides numerous advantages over conventional manual inspection of animals for determination of need for medical attention. For example, one or more embodiments of the present invention uniquely enable largely-automated early alert for a particular animal's alarming level of inactivity, which is likely to be a sign for sickness or deterioration of health. By defining an activity measurement zone (AMZ) inside or near an incentive such as food or water, and by tracking and counting the particular animal's entry to or exit from the AMZ with an RFID tag reader and an RFID tag uniquely assigned to the particular animal, various embodiments of the present invention also make proactive and early alert possible for a potential livestock disease.

Furthermore, various embodiments of this early alert system can save farmers' unnecessary manual inspection time and manpower for a large group of animals and enable them to focus on particularly alarming levels of inactivity for certain animals flagged by the early alert system. Moreover, public health may be better protected with this early alert system for livestock disease detection in livestock farms, because the early alert system is likely to prevent the spread of an infectious disease on the livestock population well before reaching the threshold point of "no return" in exponential spread of the infectious disease, as discussed in FIG. 4.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An early alert system for livestock disease detection using RFID technology, the early alert system comprising:
   an activity measurement zone (AMZ) defined by an RFID signal projection from an RFID tag reader or an RF antenna operatively connected to the RFID tag reader;
   an incentive device located near or inside the AMZ to encourage an animal attached with an RFID tag to enter and exit the AMZ periodically or frequently;
   the RFID tag reader configured to read from or write to the RFID tag attached to the animal when the animal is inside the AMZ defined by the RFID signal projection from the RFID tag reader or the RF antenna;
   a computer server with a CPU and a memory unit operatively connected to the RFID tag reader to receive and transmit information from the RFID tag attached to the animal; and an analytical program module that determines an alert trigger point in real-time by comparing an epidemic threshold point of no return for infectious disease spread in a livestock farm with an AMZ entry count for the animal over a period of time, wherein the alert trigger point is triggered for a livestock epidemic alert when a multiple number of sick animals tracked by the early alert system is approaching the epidemic threshold point of no return for infectious disease spread in the livestock farm, while the AMZ entry count for at least one animal continues to drop over a period of time, and wherein the analytical program module is executed on the CPU and the memory unit of the computer server.

2. The early alert system of claim 1, wherein the incentive device is a food dispenser system or a water feed.

3. The early alert system of claim 1, further comprising a wireless transceiver operatively connecting the computer server and the RFID tag reader for data communication.

4. The early alert system of claim 1, further comprising a user display terminal configured to display information related to the RFID tag attached to the animal, including any alerts from the analytical program module.

5. The early alert system of claim 1, wherein the computer server is a desktop computer or a laptop computer, which integrates a user display terminal.

6. The early alert system of claim 1, wherein the RFID tag is a battery-less passive tag, and wherein the RFID tag comprises a non-volatile memory unit and an embedded RF antenna unit.

7. The early alert system of claim 1, wherein the AMZ entry count is tracked and counted for the animal by the analytical program module executing on the CPU and the memory unit of the computer server.

8. The early alert system of claim 1, wherein the alert trigger point is either manually set by the user or statistically determined by the analytical program module executing on the CPU and the memory unit of the computer server.

9. The early alert system of claim 1, wherein the action of alerting the user for further medical inspection of the animal involves transmitting a phone alert, an email alert, a text message, or an alert display on a display terminal.

10. The early alert system of claim 1, wherein the RFID tag stores information comprising a unique tag identification code for the animal, a type or grade of the animal, the animal's date of birth, gender, owner, and vaccine records.

11. The early alert system of claim 10, wherein the information stored in the RFID tag further comprises an AMZ count field, which is also stored in the computer server.

12. A method of alerting a potential livestock disease to a user of an early alert system, the method comprising the steps of:

defining an activity measurement zone (AMZ) enabled by an RFID tag reader;
attaching an RFID tag to an animal, wherein the RFID tag reader can read from or write to the RFID tag when the RFID tag is within the AMZ;
activating the early alert system for livestock disease detection;
monitoring the frequency of the animal's entrance into the AMZ by accessing the RFID tag attached to the animal;
determining an alert trigger point in real-time by comparing an epidemic threshold point of no return for infectious disease spread in a livestock farm with an AMZ entry count for the animal over a period of time, wherein the alert trigger point is triggered for a livestock epidemic alert when a multiple number of sick animals tracked by the early alert system is approaching the epidemic threshold point of no return for infectious disease spread in the livestock farm, while the AMZ entry count for at least one animal continues to drop over a period of time, and wherein the step of determining the alert trigger point is generated by an analytical program executed on a CPU and a memory unit of the early alert system; and
informing the user of the early alert system to indicate that the epidemic threshold point of no return for infectious disease spread in the livestock farm is approaching, while the AMZ entry count for at least one animal is dropping.

13. The method of claim 12, wherein the step of monitoring the frequency of the animal's entrance into the AMZ involves keeping track of the AMZ entry count over a period of time in a computer server and/or the RFID tag, and comparing the AMZ entry count against the alert trigger point.

14. The method of claim 12, wherein the optional step of informing the user to encourage further inspection of the animal involves sending an alert via a display terminal, a telephone alert, an email alert, or a text message.

15. The method of claim 12, wherein the step of defining activity measurement zone (AMZ) also involves installing an incentive device inside the AMZ or nearby.

16. The method of claim 15, wherein the incentive device is a food dispenser system or a water feed.

17. The method of claim 13, wherein the step of keeping track of the AMZ entry count over the period of time and comparing the AMZ entry count against the alert trigger point are performed by an analytical program module executed on a CPU and a memory unit of the computer server operatively connected to the RFID tag reader.

* * * * *